(12) United States Patent
O'Gara

(10) Patent No.: US 8,246,998 B2
(45) Date of Patent: Aug. 21, 2012

(54) INJECTABLE BIODEGRADABLE PARTICLES

(75) Inventor: John E. O'Gara, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 838 days.

(21) Appl. No.: 12/262,835

(22) Filed: Oct. 31, 2008

(65) Prior Publication Data

US 2009/0117033 A1    May 7, 2009

Related U.S. Application Data

(60) Provisional application No. 61/001,422, filed on Nov. 1, 2007.

(51) Int. Cl.
  *A61K 9/50* (2006.01)
  *A61K 51/00* (2006.01)
(52) U.S. Cl. ................. 424/501; 424/1.11
(58) Field of Classification Search .............. None
  See application file for complete search history.

(56) References Cited

U.S. PATENT DOCUMENTS

| | | | |
|---|---|---|---|
| 4,906,476 A * | 3/1990 | Radhakrishnan | 424/450 |
| 6,350,812 B1 | 2/2002 | Vert et al. | |
| 6,521,431 B1 | 2/2003 | Kiser et al. | |
| 6,544,227 B2 | 4/2003 | Sahatjian et al. | |
| 6,626,936 B2 | 9/2003 | Stinson | |
| 2001/0021873 A1 | 9/2001 | Stinson | |
| 2003/0078339 A1 | 4/2003 | Kiser et al. | |
| 2003/0206864 A1 | 11/2003 | Mangin | |
| 2004/0197264 A1 * | 10/2004 | Schwarz et al. | 424/1.11 |
| 2004/0247624 A1 * | 12/2004 | Unger et al. | 424/400 |
| 2006/0165987 A1 * | 7/2006 | Hildgen et al. | 428/402.2 |
| 2006/0251697 A1 | 11/2006 | Li et al. | |

OTHER PUBLICATIONS

Gautier et al., J. Biomater. Sci. Polymer Edn, 2003, 14(1), pp. 63-85.*
H. Sah et al., "Development of New Microenscapsulation Techniques Useful for the Preparation of PLGA Micropsheres," Macromolecular Rapid Communications, 27 (2006), pp. 1845-1851.
K.M. Huh et al., "Synthesis and characterization of poly(ethylene glycol)/poly(L-lactic acid) alternating multiblock copolymers," Polymer, 1999, 40, pp. 6147-6155.
C. Xiao et al., "Synthesis and characterization of a Novel Degradable Aliphatic Polyester that Contains Monomeric Lactate Sequence," Macromolecular Rapid Communications, 2006, 27, pp. 637-640.

* cited by examiner

*Primary Examiner* — Brian Gulledge
(74) *Attorney, Agent, or Firm* — Mayer & Williams PC; David B. Bonham; Keum J. Park

(57) ABSTRACT

According to an aspect of the invention, injectable polymeric particles are provided that contain a copolymer that contains a hydroxy-acid-based repeat unit selected from a mono(hydroxy acid) unit and a poly(hydroxy acid) unit, an alkyl-ether-based repeat unit selected from a mono(alkyl ether) unit and a poly(alkyl ether) unit, and an acid-based repeat unit selected from a unit comprising multiple carboxylic acid groups and a derivative thereof. Other aspects of the invention pertain to methods of making such particles. Still other aspects of the invention pertain to injectable compositions that comprise such particles and to methods of treatment that employ such injectable compositions.

24 Claims, No Drawings

INJECTABLE BIODEGRADABLE PARTICLES

STATEMENT OF RELATED APPLICATIONS

This application claims the benefit of U.S. Provisional Patent Application Ser. No. 61/001,422, filed Nov. 1, 2007, entitled "Injectable Biodegradable Particles", which is incorporated by reference herein in its entirety.

FIELD OF THE INVENTION

The invention relates to polymeric particles for injection.

BACKGROUND OF THE INVENTION

Many clinical situations benefit from regulation of the vascular, lymphatic or duct systems by restricting the flow of body fluid or secretions. For example, the technique of embolization involves the introduction of particles into the circulation to occlude blood vessels, for example, so as to either arrest or prevent hemorrhaging or to cut off blood flow to a structure or organ. Permanent or temporary occlusion of blood vessels is desirable for managing various diseases and conditions.

In a typical embolization procedure, local anesthesia is first given over a common artery. The artery is then percutaneously punctured and a catheter is inserted and fluoroscopically guided into the area of interest. An angiogram is then performed by injecting contrast agent through the catheter. An embolic agent is then deposited through the catheter. The embolic agent is chosen, for example, based on the size of the vessel to be occluded, the desired duration of occlusion, and/or the type of disease or condition to be treated, among others factors. A follow-up angiogram is usually performed to determine the specificity and completeness of the arterial occlusion.

Various polymer-based microspheres are currently employed to embolize blood vessels. These microspheres are usually introduced to the location of the intended embolization through microcatheters. Many commercially available embolic microspheres are composed of polymers. Materials commonly used commercially for this purpose include polyvinyl alcohol (PVA), acetalized PVA (e.g., Contour SE™ embolic agent, Boston Scientific, Natick, Mass., USA) and crosslinked acrylic hydrogels (e.g., Embospheres®, Biosphere Medical, Rockland, Mass., USA). Similar microspheres have been used in chemoembolization to increase the residence time of the therapeutic after delivery. In one specific instance, a therapeutic agent (doxorubicin) has been directly added to polyvinyl alcohol hydrogel microspheres such that it can be released locally after delivery (e.g., DC Bead™ drug delivery chemoembolization system, Biocompatibles International plc, Farnham, Surrey, UK). Other examples of commercially available microspheres include glass microspheres with entrapped radioisotopes (e.g., $^{90}Y$), in particular, TheraSpheres™, MDS Nordion, Ottowa, Canada and polymer microspheres that contain monomers that are capable of chelating radioisotopes ($^{90}Y$), in particular, SIR-Spheres®, SIRTex Medical, New South Wales, Australia.

Currently, the only commercial biodegradable embolic material is GelFoam. Although used clinically, the material has the disadvantage that it is not available in a spherical form, which can lead to problems and variability during delivery through microcatheters. A spherical embolic material that is degradable would thus be attractive since it would have the benefits of the microsphere based materials such as a physician's familiarity with microsphere handling and delivery as well as a longer and more flexible time period to handle and deliver the embolic material, while also possessing the capability of biodegrading over time in vivo, which is beneficial, for example, because the vasculature of the structure or organ being treated (e.g., tumor, etc.) may be accessed for additional treatments at a later time and/or because of reduced risk of complications or patient objections arising from a permanently implanted material.

It is also known to use polymer-based microspheres as augmentative materials for aesthetic improvement, including improvement of skin contour. Furthermore, polymer-based microspheres have also been used as augmentative materials in the treatment of various diseases, disorders and conditions, including urinary incontinence, vesicourethral reflux, fecal incontinence, intrinsic sphincter deficiency (ISD) and gastroesophageal reflux disease, among others. For instance, a common method for treating patients with urinary incontinence is via periurethral or transperineal injection of a bulking agent that contains polymer-based microspheres. In this regard, methods of injecting bulking agents for treatment of urinary incontinence commonly require the placement of a needle at a suitable treatment region, for example, periurethrally or transperineally. The bulking agent is injected into a plurality of locations, assisted by visual aids, causing the urethral lining to coapt. Commercially available bulking agents are typically biostable.

SUMMARY OF THE INVENTION

In accordance with one aspect of the invention, biodegradable injectable polymeric particles are provided that contain a copolymer that contains a hydroxy-acid-based repeat unit selected from a mono(hydroxy acid) unit and a poly(hydroxy acid) unit, an alkyl-ether-based repeat unit selected from a mono(alkyl ether) unit and a poly(alkyl ether) unit, and an acid-based repeat unit selected from a unit comprising multiple carboxylic acid groups and derivatives thereof.

Other aspects of the invention pertain to methods of making such particles. Still other aspects of the invention pertain to injectable compositions that comprise such particles and to methods of treatment that employ such injectable compositions.

These and various additional aspects, embodiments and advantages of the present invention will become immediately apparent to those of ordinary skill in the art upon review of the Detailed Description and any appended claims to follow.

DETAILED DESCRIPTION

In accordance with one aspect of the invention, injectable biodegradable polymeric particles are provided that contain a copolymer that contains a hydroxy-acid-based repeat unit selected from a mono(hydroxy acid) unit and a poly(hydroxy acid) unit, an alkyl-ether-based repeat unit selected from a mono(alkyl ether) unit and a poly(alkyl ether) unit, and an acid-based repeat unit selected from a unit comprising multiple carboxylic acid groups and derivatives thereof (e.g., multiple acid chloride groups, an acid anhydride unit, etc.).

As used herein a "polymeric particle" is one that contains polymers, for example, from 50 wt % or less to 75 wt % to 90 wt % to 95 wt % to 97.5 wt % to 99 wt % or more polymers.

As used herein a "biodegradable polymeric particle" is one that undergoes chain cleavage in vivo.

As used herein, "polymers" are molecules that contain multiple copies of one or more types of constitutional species, commonly referred to as monomers. The number of monomers within a given polymer may vary widely, ranging, for example, from 5 to 10 to 25 to 50 to 100 to 1000 to 10,000 or more constitutional units. As used herein, the term "monomers" may refer to the free monomers and those that are incorporated into polymers (also referred to herein as monomer "residues"), with the distinction being clear from the context in which the term is used.

Polymers in accordance with the present invention contain various repeat "units" (i.e., incorporated monomers or blocks of monomers), which units can be, for example, hydroxy-acid-based repeat units selected from mono(hydroxy acid) units and poly(hydroxy acid) units (also referred to herein as "hydroxy-acid-based residues"), alkyl-ether-based repeat units selected from mono(alkyl ether) units and poly(alkyl ether) units (also referred to herein as "alkyl-ether-based residues"), and acid-based repeat units selected from selected from units comprising multiple carboxylic acid groups and derivatives thereof, including units comprising multiple acid-chloride groups and cyclic anhydride units (also referred to herein as "acid-based residues").

Alkyl-ether-based repeat units for use in the present invention include mono(alkyl ether) and poly(alkyl ether) units, which may contain one or more types —$R_1$—O— monomers, where in the preceding formula $R_1$ is alkyl, for example, C1-C10 alkyl, which may be linear or branched, for example, repeat units of the formula $-[R_1-O]_n-$, where n in the preceding formula is an integer of 1 or more ranging, for example, from 1 to 2 to 5 to 10 to 25 to 50 to 100 to 250 to 500 to 1000 or more. A few specific examples of alkyl-ether-based units include those of the formula $-[CH_2CH_2-O]_n-$, which is referred to as an ethylene glycol unit (where n=1), an ethylene oxide unit (where n=1), a polyethylene glycol unit (where n>1) or as polyethylene oxide (where n>1), —[$CH_2CH(CH_3)$—O$]_n$—, which is referred to as a propylene glycol unit (where n=1), a propylene oxide unit (where n=1), a polypropylene glycol unit (where n>1) or a polypropylene oxide (where n>1), and $-[(CH_2)_4-O]_n-$, which is referred to as a tetramethylene glycol unit (where n=1), a butylene oxide unit (where n=1), a polytetramethylene glycol unit (where n>1) or a polybutylene oxide unit (where n>1), among many others.

Hydroxy-acid-based repeat units for use in the present invention include mono(hydroxy acid) and poly(hydroxy acid) repeat units, which may contain one or more types of hydroxy acid monomers selected, for example, branched and unbranched C1-C10 hydroxy acids, typically monomers having a single hydroxyl group and a single carboxyl group, including hydroxyacetic acids such as alpha-hydroxy acetic acid (glycolic acid), hydroxypropionic acids such as alpha-hydroxypropionic acid (lactic acid) and beta-hydroxypropionic acid, hydroxybutyric acids such as alpha-hydroxybutyric acid, beta-hydroxybutyric acid and gamma-hydroxybutyric acid, hydroxyvaleric acids such as alpha-hydroxyvaleric acid, beta-hydroxyvaleric acid, gamma-hydroxyvaleric acid and delta-hydroxyvaleric acid, hydroxycaproic acids such as alpha-hydroxycaproic acid, beta-hydroxycaproic acid, gamma-hydroxycaproic acid, delta-hydroxycaproic acid and epsilon-hydroxycaproic acid, as well as various hydroxyheptanoic acids, various hydroxyoctanoic acids, various hydroxynananoic acids and various hydroxydecanoic acids, among many others. In certain embodiments, the hydroxy acid repeat unit is of the formula

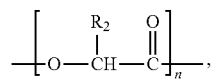

where in the preceding formula $R_2$ is H or alkyl, for example, C1-C10 alkyl, which may be linear or branched, and n is an integer of 1 or more, for example, ranging from 1 to 2 to 5 to 10 to 25 to 50 to 100 to 250 to 500 to 1000 or more. Many of the forgoing monomers are chiral. Thus, where two or more of the same chiral monomer are in the hydroxyl repeat unit, the monomers may be l-monomers, d-monomers or a mixture of l- and d-monomers (e.g., l-lactide, d-lactide or d,l-lactide monomers among others).

Acid-based repeat units for use in the present invention may be selected from units comprising multiple carboxylic acid groups and their derivatives, including, for example, di-carboxylic acids, tri-carboxylic acids, di-acid chlorides, tri-acid chlorides and cyclic acid anhydrides, among others.

Examples of di-carboxylic acid units include, for example, residues of oxalic acid and di-carboxyl-substituted C1 to C10 alkanes, which may be linear or branched, which alkanes may be further substituted, for example, with one or more halogen atoms (e.g., fluoro, chloro, bromo and/or iodo groups). Specific examples of di-carboxyl-substituted C1 to C10 alkanes include malonic acid(methanedicarboxylic acid), succinic acid(1,2-ethanedicarboxylic acid), glutaric acid(1,3-propanedicarboxylic acid), adipic acid(1,4-butanedicarboxylic acid), pimelic acid(1,5-pentanedicarboxylic acid), suberic acid(1,6-hexanedicarboxylic acid), azelaic acid(1,7-heptanedicarboxylic acid), and sebacic acid(1,8-octanedicarboxylic acid), most of which are alpha,omega-di-carboxylic-acid substituted linear alkanes, which alkanes may be substituted with one or more halogen atoms in some embodiments.

Examples of tri-carboxylic acid units further include, for example, residues of tri-carboxyl-substituted C1 to C10 alkanes, which may be linear or branched, which alkanes may be further substituted, for example, with one or more halogen groups. Specific examples of tri-carboxyl-substituted C2 to C10 alkanes include tricarballylic acid(1,2,3-propanetricarboxylic acid), 1,2,3-butanetricarboxylic acid, 1,2,4-butanetricarboxylic acid and so forth, which alkanes may be substituted with one or more halogen atoms in some embodiments.

Examples of cyclic acid anhydride units include, for example, residues of anhydrides of di-carboxyl-substituted C1 to C10 alkanes (which alkanes may be linear or branched, and which alkanes may be further substituted, for example, with one or more halogen groups). Specific examples include malonic anhydride, succinic anhydride, glutaric anhydride, adipic anhydride, pimelic anhydride, suberic anhydride, azelaic anhydride, sebacic anhydride, and so forth, as well as derivatives of the same in which one or more methylene groups are substituted with one or more halogen groups.

Examples of di-acid chloride units include, for example, residues of oxalic acid dichloride (oxalyl chloride, also referred to as oxalyl dichloride) and di-acid-chloride-substituted C1 to C10 alkanes, which may be linear or branched, which alkanes may be further substituted, for example, with one or more halogen atoms. Specific examples of di-acid-chloride-substituted C1 to C10 alkanes include malonic acid dichloride (propanedioyl dichloride), succinic acid dichloride (butanedioyl dichloride), glutaric acid dichloride (pentanedioyl dichloride), adipic acid dichloride (hexanedioyl dichloride), pimelic acid dichloride (heptanedioyl dichloride), suberic acid dichloride (octanedioyl dichloride), azelaic acid dichloride (nonanedioyl dichloride), and sebacic acid dichloride (decanedioyl dichloride), most of which are alpha,omega-acid-chloride substituted linear alkanes.

In certain embodiments, acid-based repeat units for use in the present invention may be of the formula,

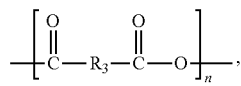

where in the preceding formula n is an integer of one or more, for example, ranging from 1 to 2 to 5 to 10 to 25 to 50 to 100 to 250 to 500 to 1000 or more, and $R_3$ is selected from (a) a bond (e.g., in the case of oxalic acid or oxalyl chloride) and (b) C1-C10 alkyl, which may be linear or branched, and which may be unsubstituted or substituted with one or more halogen atoms.

Bromine and iodine atoms are preferred as halogen groups in some embodiments, for purposes of increasing the radiopacity of the polymer (i.e., making the polymer more absorptive of x-rays and thus more visible under x-ray imaging techniques such as x-ray fluoroscopy, among others). One specific example of a brominated polyacid, among many others, is bromo-succinic acid. One specific example of a brominated anhydride, among many others, is bromo-succinic anhydride.

In other embodiments, a separate radiopacifying agent may be added to the injectable particles of the invention. Examples of radiopacifying agents include metals, metal salts and metal oxides, and iodinated compounds. More specific examples of such agents include gold, tungsten, platinum, tantalum, iridium, or other dense metal, barium sulfate, bismuth subcarbonate, bismuth trioxide, bismuth oxychloride, metrizamide, iopamidol, iothalamate sodium, iodomide sodium, and meglumine.

The injectable particles of the invention may be non-crosslinked or they may be covalently and/or non-covalently crosslinked. Thus, in some embodiments, crosslinking agents such as covalent crosslinking agents or ionic crosslinking agents may be present in the injectable particles, whereas in other embodiments crosslinking agents are absent from the particles. In some embodiments the particles may be crosslinked by exposure to radiation (e.g., gamma or e-beam radiation), which may occur in conjunction with sterilization of particles.

The injectable particles may be used to treat various diseases and conditions in a variety of subjects. Subjects include vertebrate subjects, particularly humans and various warm-blooded animals, including pets and livestock. As used herein, "treatment" refers to the prevention of a disease or condition, the reduction or elimination of symptoms associated with a disease or condition, or the substantial or complete elimination of a disease or condition. Preferred treatments include embolization and tissue bulking.

The injectable particles of the invention may vary in shape. In certain embodiments, they are substantially spherical, for example, having the form of a perfect (to the eye) sphere or the form of a near-perfect sphere such as a prolate spheroid (a slightly elongated sphere) or an oblate spheroid (a slightly flattened sphere), among other regular or irregular near-spherical geometries. In embodiments where the particles are substantially spherical, at least half of the particles (50% or more, for example, from 50% to 75% to 90% to 95% or more of a particle sample) may have a sphericity of 0.8 or more (e.g., from 0.80 to 0.85 to 0.9 to 0.95 to 0.97 or more). The sphericity of a collection of particles can be determined, for example, using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures the particles in an image. The sphericity of a particle, which is computed as Da/Dp (where $Da=\sqrt{(4A/\pi)}$; $Dp=P/\pi$; A=pixel area; P=pixel perimeter), is a value from zero to one, with one representing a perfect circle.

The injectable particles of the invention can vary significantly in size, with typical longest linear cross-sectional dimensions (e.g., the diameter of a sphere, the length of a fiber, etc.) ranging, for example, from 40 to 50 to 100 to 150 to 250 to 500 to 750 to 1000 to 1500 to 2000 to 2500 to 5000 microns (μm). Where collections of microspheres are employed at least 95 vol % of the population will fall within these ranges.

Particles for use in the present invention include porous and non-porous particles. As used herein, a "porous particle" is one that contains pores, which may be observed, for example, by viewing the injectable particles using a suitable microscopy technique such as scanning electron or optical microscopy. Porous particles may be porous throughout or may be partially porous, for example, comprising a non-porous core with a porous outer layer. Pore size may vary widely, ranging from 1 micron or less to 2 microns to 5 microns to 10 microns to 25 microns to 50 microns to 100 microns or more in width. Pores can be present in a wide range of shapes. Pores may be formed, for example, through the use of poragens or through freeze-thaw cycling, among other methods.

In certain embodiments of the invention, the injectable particles may be hydrogel particles. As used herein, a "hydrogel" particle is a crosslinked polymer particle that swells when placed in water or biological fluids, but remains insoluble at least for a time. For instance, a hydrogel particle in accordance with the invention may undergo swelling in water such that its longest linear cross-sectional dimension (e.g., for a sphere, the diameter) increases by 5% or less to 10% to 15% to 20% to 25% or more. In the present invention, the insolubility of the hydrogel is not permanent, and the particles biodisintegrate in vivo.

In some embodiments, the injectable particle compositions in accordance with the invention further comprise one or more therapeutic agents. The therapeutic agents may be provided on, within, and/or external to the particles, depending on the embodiment.

"Therapeutic agents," "biologically active agents," "drugs," "pharmaceutically active agents," "pharmaceutically active materials," and other related terms may be used interchangeably herein and include genetic therapeutic agents, non-genetic therapeutic agents and cells. Numerous therapeutic agents can be employed in conjunction with the present invention, including those used for the treatment of a wide variety of diseases and conditions (i.e., the prevention of a disease or condition, the reduction or elimination of symptoms associated with a disease or condition, or the substantial or complete elimination of a disease or condition). Numerous therapeutic agents are described here.

Examples of therapeutic agents which may be used in the compositions of the invention for embolic applications include toxins (e.g., ricin toxin, radioisotopes, or any other agents able to kill undesirable cells, such as those making up cancers and other tumors such as uterine fibroids) and agents that arrest growth of undesirable cells.

Specific examples of therapeutic agents may be selected from suitable members of the following: radioisotopes including $^{90}$Y, $^{32}$P, $^{18}$F, $^{140}$La, $^{153}$Sm, $^{165}$Dy, $^{166}$Ho, $^{169}$Er, $^{169}$Yb, $^{177}$Lu, $^{186}$Re, $^{188}$Re, $^{103}$Pd, $^{198}$Au, $^{192}$Ir, $^{90}$Sr, $^{111}$In or $^{67}$Ga, antineoplastic/antiproliferative/anti-miotic agents including antimetabolites such as folic acid analogs/antagonists (e.g., methotrexate, etc.), purine analogs (e.g., 6-mercaptopurine, thioguanine, cladribine, which is a chlorinated purine nucleoside analog, etc.) and pyrimidine analogs (e.g., cytarabine, fluorouracil, etc.), alkaloids including taxanes (e.g., paclitaxel, docetaxel, etc.), alkylating agents such as alkyl sulfonates, nitrogen mustards (e.g., cyclophosphamide, ifosfamide, etc.), nitrosoureas, ethylenimines and methylmelamines, other aklyating agents (e.g., dacarbazine, etc.), antibiotics and analogs (e.g., daunorubicin, doxorubicin, idarubicin, mitomycin, bleomycins, plicamycin, etc.), platinum complexes (e.g., cisplatin, carboplatin, etc.), antineoplastic enzymes (e.g., asparaginase, etc.), agents affecting microtubule dynamics (e.g., vinblastine, vincristine, colchicine, Epo D, epothilone), caspase activators, proteasome inhibitors, angiogenesis inhibitors (e.g., statins such as endostatin, cerivastatin and angiostatin, squalamine, etc.), rapamycin (sirolimus) and its analogs (e.g., everolimus, tacrolimus, zotarolimus, etc.), etoposides, and many others (e.g., hydroxyurea, flavopiridol, procarbizine, mitoxantrone, campothecin, etc.), various pharmaceutically acceptable salts and derivatives (e.g., esters, etc.) of the foregoing, and combinations of the foregoing, among other agents.

Further therapeutic agents include thrombogenic agents such as homocysteine.

Further therapeutic agents include chemical ablation agents (materials whose inclusion in the formulations of the present invention in effective amounts results in necrosis or shrinkage of nearby tissue upon injection) including osmotic-stress-generating agents (e.g., salts, etc.). Specific examples of chemical ablation agents from which suitable agents can be selected include the following: basic agents (e.g., sodium hydroxide, potassium hydroxide, etc.), acidic agents (e.g., acetic acid, formic acid, etc.), enzymes (e.g., collagenase, hyaluronidase, pronase, papain, etc.), free-radical generating agents (e.g., hydrogen peroxide, potassium peroxide, etc.), other oxidizing agents (e.g., sodium hypochlorite, etc.), tissue fixing agents (e.g., formaldehyde, acetaldehyde, glutaraldehyde, etc.), coagulants (e.g., gengpin, etc.), non-steroidal anti-inflammatory drugs, contraceptives (e.g., desogestrel, ethinyl estradiol, ethynodiol, ethynodiol diacetate, gestodene, lynestrenol, levonorgestrel, mestranol, medroxyprogesterone, norethindrone, norethynodrel, norgestimate, norgestrel, etc.), GnRH agonists (e.g, buserelin, cetorelix, decapeptyl, deslorelin, dioxalan derivatives, eulexin, ganirelix, gonadorelin hydrochloride, goserelin, goserelin acetate, histrelin, histrelin acetate, leuprolide, leuprolide acetate, leuprorelin, lutrelin, nafarelin, meterelin, triptorelin, etc.), anti-progestogens (e.g., mifepristone, etc.), selective progesterone receptor modulators (SPRMs) (e.g., asoprisnil, etc.), various pharmaceutically acceptable salts and derivatives of the foregoing, and combinations of the foregoing, among other agents.

For tissue bulking applications (e.g., urethral bulking, cosmetic bulking, etc.), specific beneficial therapeutic agents include those that promote collagen production, including proinflammatory agents and sclerosing agents such as those listed Pub. No. US 2006/0251697.

Proinflammatory agents can be selected, for example, from suitable endotoxins, cytokines, chemokines, prostaglandins, lipid mediators, and other mitogens. Specific examples of proinflammatory agents from which suitable agents can be selected include the following: growth factors such as platelet derived growth factor (PDGF), fibroblast growth factor (FGF), transforming growth factor (such as TGF-alpha and TGF-beta), epidermal growth factor (EGF), insulinlike growth factor (IGF), interleukins such as IL-1-(alpha or beta), IL-8, IL-4, IL6, IL-10 and IL-13, tumor necrosis factor (TNF) such as TNF-alpha, interferons such as INF-gamma, macrophage inflammatory protein-2 (MIP-2), leukotrienes such as leukotriene B4 (LTB4), granulocyte macrophage-colony stimulating factor (GM-CSF), cyclooxygenase-1, cyclooxygenase-2, macrophage chemotactic protein (MCP), inducible nitric oxide synthetase, macrophage inflammatory protein, tissue factor, phosphotyrosine phosphates, N-formyl peptides such as formyl-Met-Leu-Phe (fMLP), second mitochondria-derived activator of caspase (sMAC), activated complement fragments (C5a, C3a), phorbol ester (TPA), superoxide, hydrogen peroxide, zymosan, bacterial lipopolysaccharide, imiquimod, various pharmaceutically acceptable salts and derivates of the foregoing, and combinations of the foregoing, among other agents.

Suitable sclerosing agents for the practice of the invention can be selected, for example, from the following: inorganic materials such as aluminum hydroxide, sodium hydroxide, silver nitrate and sodium chloride, as well as organic compounds, including alcohols such as ethanol, acetic acid, trifluoroacetic acid, formaldehyde, dextrose, polyethylene glycol ethers (e.g., polidocanol, also known as laureth 9, polyethylene glycol (9) monododecyl ether, and hydroxypolyethoxydodecane), tetracycline, oxytetracycline, doxycycline, bleomycin, triamcinolone, minocycline, vincristine, iophendylate, tribenoside, sodium tetradecyl sulfate, sodium morrhuate, diatrizoate meglumine, prolamine diatrizoate, alkyl cyanoacrylates such as N-butyl-2-cyanoactyalte and methyl 2-cyanoacrylate, ethanolamine, ethanolamine oleate, bacterial preparations (e.g., corynebacterium and streptococcal preparations such as picibanil) and mixtures of the same, among others.

The amount of therapeutic agent within the compositions of the present invention will vary widely depending on a number of factors, including the disease or condition being treated, the potency of the therapeutic agent, and the volume of particulate composition that is ultimately injected into the subject, among other factors, with the therapeutically effective amount being readily determined by those of ordinary skill in the art. Where a therapeutic agent is provided within the compositions of the present invention, typical loadings range, for example, from 0.1 wt % or less, to 0.2 wt % to 0.5 wt % to 1 wt % to 2 wt % to 5 wt % to 10 wt % to 20 wt % or more of the dry weight of the composition.

In some embodiments, particles in accordance with the present invention may be provided with one or more binding groups that specifically or non-specifically interact with a therapeutic agent, for example, in order to retard the release of the therapeutic agent. For instance, such binding groups may be provided within the copolymers described herein (e.g., covalently bonded via reaction with the hydroxyl or carboxyl groups of the copolymers) or within an optional supplemental polymer that may be present in the particles. Such binding groups may interact with the therapeutic agent via any of a variety of mechanisms, for example, based on non-covalent interactions such as van der Waals forces, hydrophobic interactions and/or electrostatic interactions (e.g., charge-charge interactions, charge-dipole interactions, and dipole-dipole interactions, including hydrogen bonding). Examples of specific non-covalent interactions include $\pi$-$\pi$ stacking, binding based on the formation of multiple hydrogen bonds (e.g., polynucleotide hybridization, etc.), binding based on the formation of complexes and/or coordinative bonds (e.g., metal ion chelation, etc.), binding based on antibody-antigen interactions, also sometimes referred to as antibody-hapten interactions, protein-small molecule interactions (e.g., avidin/streptavidin-biotin binding), protein-protein interactions, and so forth.

As a specific example, where particulate compositions comprising radioisotopes are formed, it is desirable in some embodiments to provide the particles with one or more binding groups that interact with the radioisotopes via an electrostatic-based interaction such as ion exchange, complexation, coordination, chelation, etc. For instance, ligands possessing functional groups such as carbonyls and thiols may be provided within the particles (e.g., within the copolymers described herein or within a supplemental polymer that may be optionally included in the particles), which ligands are capable of forming coordination compounds (e.g., chelates) with charged radioactive ions. An approach of this type is beneficial in that the polymers forming the particles need not be exposed to the high energy radiation that is associated with the conversion of non-radioactive species (e.g., $^{89}$Y) to radioactive species (e.g., $^{90}$Y). Instead, the particles can be loaded with the radioactive species after it is exposed to the high energy radiation. The exposure of most polymers to the levels of radiation needed to convert non-radioactive isotopes to radioactive would be expected to result in significant damage to the polymer (e.g., extensive chain scission and or crosslinking) resulting in modifications to the mechanical properties of the polymers, among other changes.

As noted above, in accordance one aspect, the invention provides injectable polymeric particles that contain a copolymer that contains a hydroxy-acid-based repeat unit selected from a mono(hydroxy acid) unit and a poly(hydroxy acid) unit, an alkyl-ether-based repeat unit selected from a mono(alkyl ether) unit and a poly(alkyl ether) unit, and an acid-based repeat unit selected from units comprising multiple carboxylic acid groups and derivatives thereof.

Several specific polymers suitable for the practice of the invention will now be discussed, along with methods for their formation.

In a recent publication, Xiao et al. describe the synthesis of a degradable polyester that contains repeating lactic acid, ethylene glycol, and succinic anhydride monomeric sequences. See *Macromolecular Rapid Communications*, 2006, 27, 637-640. In this paper, the authors first reacted lactic acid with ethylene glycol to form ethylene glycol lactate diol as follows:

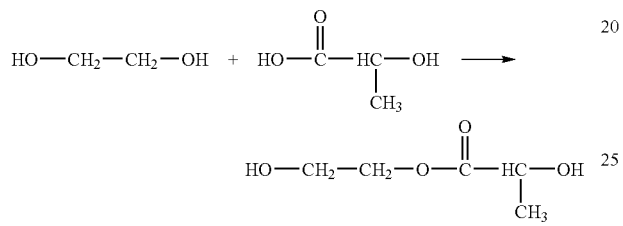

This diol is then reacted with succinic anhydride

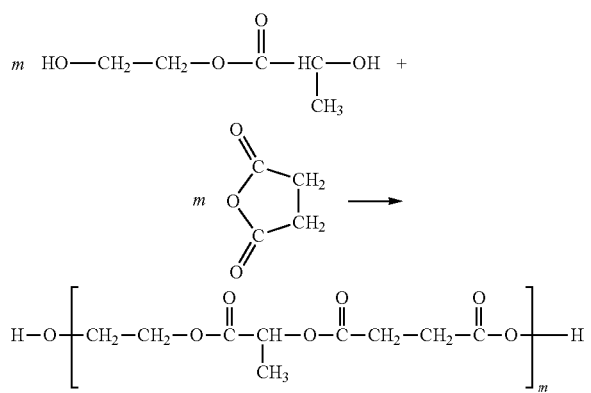

where m in the preceding formula is an integer. The molecular weight of the thus formed product was increased by removing the reaction byproduct ($H_2O$) under vacuum. The final copolymer thus contains each of the ethylene glycol, lactic acid, and succinic anhydride repeat units are in a 1:1:1 molar ratio. The copolymer is synthesized without the use of toxic metal catalysts.

Such polymers are suitable for use in the embolic particles of the present invention. Moreover, in the present invention, variations on this process may be employed in which other hydroxy acid and alkylene glycol monomers may be used, as well as macro-monomers (macromers) of the same. For example, in the first step (a) the following hydroxyacid monomers may be employed,

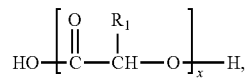

where in the preceding formula $R_1$ is hydrogen or an alkyl group (e.g., C1-C10 linear or branched alkyl) and x is an integer of 1 or more and (b) the following alkylene glycol monomers may be employed,

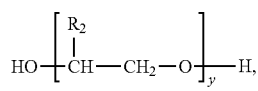

where in the preceding formula $R_2$ is hydrogen or an alkyl group (e.g., C1-C10 linear or branched alkyl) and y is an integer of 1 or more, to yield a monomer such as the following for use in the second step:

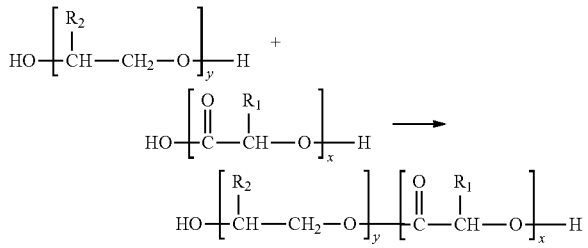

Thus, monomers for use in the second step may be selected from the following: (a) mono(hydroxyacid)-mono(alkylene glycol) diol monomers, (b) poly(hydroxyacid)-mono(alkylene glycol) diol macromers, (c) mono(hydroxy acid)-poly(alkylene glycol) diol macromers, and (d) poly(hydroxyacid)-poly(alkylene glycol) diol macromers. Another variation on this process would be to use additional cyclic anhydrides in the second step, for example,

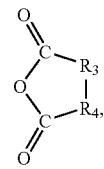

where $R_3$ and $R_4$ in the preceding formula are independently alkyl or halo alkyl (e.g., unsubstituted or halo-substituted C1-C10 alkyl, which may be linear or branched), yielding a polymer along the following lines, where m is an integer:

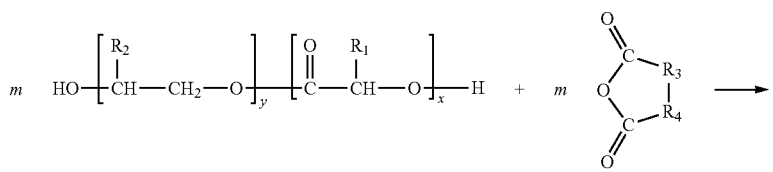

-continued

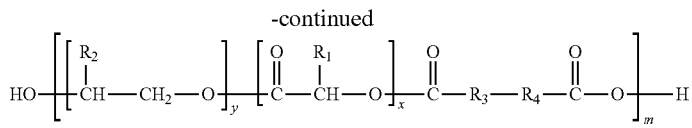

The molar ratio of the three repeat units, i.e., mono or poly(hydroxy acid) to diacid anhydride to mono or poly(alkylene oxide), is 1 to 1 to 1. Examples of chemical variations for this structure, include an increase in molecular weight (e.g., by increasing x, y and/or m), a decrease in molecular weight (e.g., by decreasing x, y and/or m), a variation in the mono or poly(hydroxy acid) unit (e.g., by variation of $R_1$), a variation in the mono or poly(alkylene oxide) unit (e.g., by variation of $R_2$) or a variation in the acid anhydride unit (e.g., by variation of $R_3$ and/or $R_4$). In one embodiment, $R_1$ is H and the hydroxy-acid-based repeat unit is glycolide or polyglycolide. In another embodiment, $R_1$ is $CH_3$ and the hydroxy-acid-based repeat unit is lactide or polylactide. In one embodiment, $R_2$ is H and the alkylene-oxide-based repeat unit is ethylene oxide or poly(ethylene oxide). In another embodiment, $R_2$ is $CH_3$ and the alkylene-oxide-based repeat unit is propylene oxide or poly(propylene oxide). In one embodiment, $R_3$ and $R_4$ are both —$CH_2$— and the multi-acid-based repeat unit is succinic anhydride. In another embodiment, $R_3$ and $R_4$ are both —$CH_2CH_2CH_2CH_2$— and the multi-acid-based repeat unit is sebacic acid anhydride. In another embodiment, $R_3$ is —$CH_2$— and $R_4$ is —CHBr— and the multi-acid-based repeat unit is bromosuccinic anhydride.

In the polymer synthesis, the acid-based repeat unit may also be derived from an alpha,omega-dicarboxylic acid substituted alkane, with a dehydrating agent being used to achieve coupling of an alcohol functionality with the acid functionality of the dicarboxylic acid molecule, thereby creating an ester linkage.

Huh and Bae have described the synthesis of a degradable, multiblock aliphatic polyester that contains poly(L-lactide) sequences (*Polymer*, 1999, 40, 6147-6155). In this paper, the authors polymerize L-lactic acid in the presence of succinic acid to form the following polymer

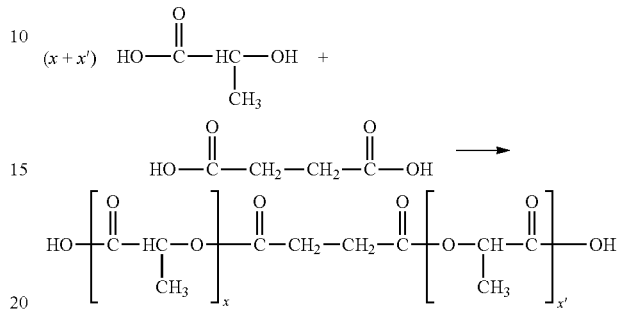

where x and x' in the preceding formula are integers. This polymer was then used as a macromonomer, along with polyethylene glycol, in the following polycondensation reaction using dicyclohexyl carbodiimide and N-dimethyl aminopyridine as catalysts:

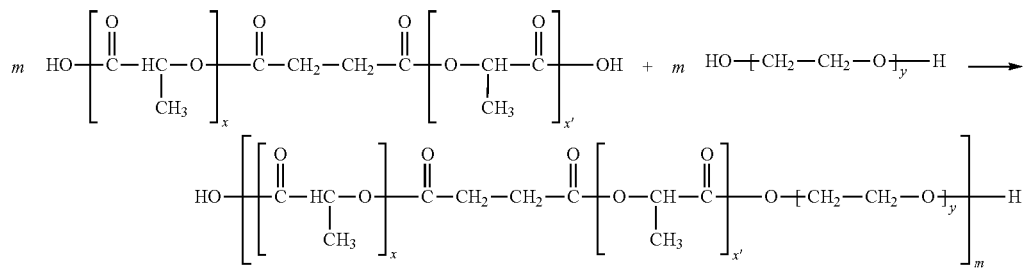

where m and y in the preceding formula are independent integers. The molar ratio of the three repeat units in this copolymer (polylactic acid:succinic acid:polyethylene glycol) is 2:1:1, respectively. The polymer is synthesized without the use of toxic metal catalysts.

This copolymer is suitable for use in the embolic particles of the present invention. Moreover, variations of this copolymer, based on other hydroxy-acid-based repeat units, other alkyl-ether-based repeat units and/or other acid-based repeat units, may be used in the particles of the invention. For example, copolymers for use in the invention may be formed along the following lines:

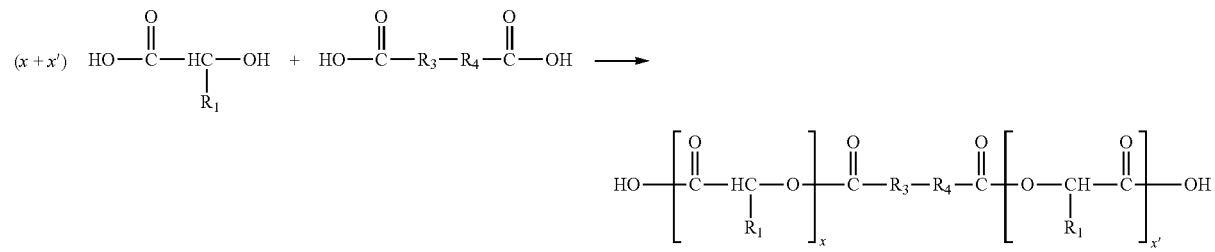

-continued

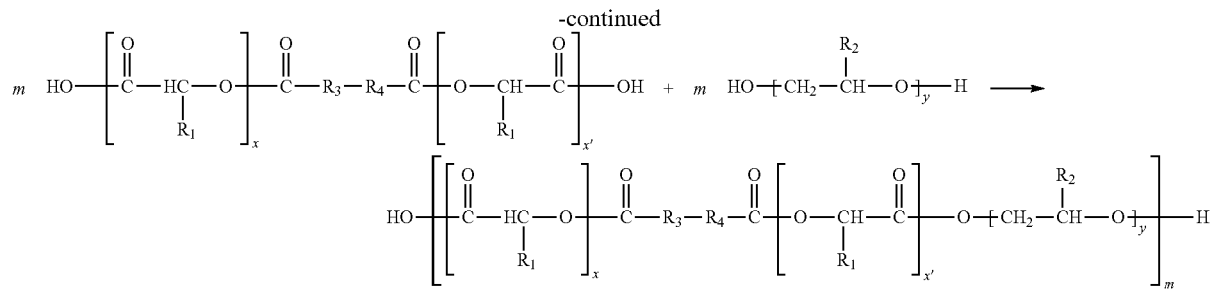

where in the preceding formula x, x', y and m are independently (although the values x and x' will typically not vary significantly from one another) integers of 2 or more, typically significantly more than 2 (e.g., 2 to 5 to 10 to 25 to 50 to 100 or more), where in the preceding formula $R_1$ and $R_2$ are, independently, hydrogen or an alkyl group (e.g., C1-C10 linear or branched alkyl), and where in the preceding formula $R_3$ and $R_4$ are, independently, alkyl or haloalkyl groups (e.g., C1-C10 alkyl or C1-C10 haloalkyl). The molar ratio of the three repeat units (polyhydroxyacid:diacid:polyalkylene oxide) is 2:1:1, respectively. Examples of chemical variations for this structure include an increase in molecular weight (e.g., by increasing x, x', y and/or m), a decrease in molecular weight (e.g., by decreasing x, x', y and/or m), a variation in the poly(hydroxyacid) unit (e.g., by variation of $R_1$), a variation in the poly(alkylene oxide) unit (e.g., by variation of $R_2$) or by variation in the acid anhydride unit (e.g., by variation of $R_3$ and/or $R_4$). In one embodiment, $R_1$ is H and the hydroxy-acid-based repeat unit is polyglycolide. In another embodiment, $R_1$ is $CH_3$ and the hydroxy-acid-based repeat unit is polylactide. In one embodiment, $R_2$ is H and the alkylene-oxide-based repeat unit is poly(ethylene oxide). In another embodiment, $R_2$ is $CH_3$ and the alkylene-oxide-based repeat unit is poly(propylene oxide). In one embodiment, $R_3$ and $R_4$ are both —$CH_2$— and the acid-based repeat unit is succinic acid. In another embodiment, $R_3$ and $R_4$ are both —$CH_2CH_2CH_2CH_2$— and the multi-acid-based repeat unit is sebacic acid. In another embodiment, $R_3$ is —$CH_2$— and $R_4$ is —CHBr— and the multi-acid-based repeat unit is bromosuccinic acid.

Copolymers formed using the above and other synthesis techniques may then be subjected to suitable isolation and purification techniques, as appropriate.

Particles suitable for injection (e.g., for embolic, bulking or other purposes) can be prepared using any suitable technique, for example, solvent evaporation based methods or droplet generator type methods, among others.

For example, in solvent evaporation based methods, a copolymer from which the particles are to be formed is dissolved in a water-immiscible, volatile organic solvent such as methylene chloride or chloroform. This solution is subsequently added to a larger volume of an aqueous solution containing a stabilizing compound (e.g., polyvinyl alcohol, poloxamer, gelatin, etc.) and the resulting mixture mechanically agitated (e.g., by homogenization, sonication, vortexing etc.) to form an emulsion in which the dispersed phase comprises the polymer dissolved in the organic solvent. The organic solvent is then evaporated, leaving behind a suspension of solid polymer particles.

In some embodiments, it may be desirable to introduce one or more optional agents, such as therapeutic agents, radiopacifying agents or optional polymers, into the particles during the particle formation process. For example, the one or more optional agents may be dissolved or dispersed in the organic solvent along with the polymer. In an alternative technique, known as the water-in-oil-in-water (W/O/W) technique, the one or more optional agent may be dissolved in an aqueous solution which is added to a larger volume of the polymer solution containing the volatile organic solvent. This mixture is then mechanically agitated to form a primary emulsion, which is then added to an even larger volume of an aqueous solution containing a stabilizing compound. This mixture is then mechanically agitated to form a secondary (W/O/W) emulsion. The volatile organic solvent is then evaporated as above.

In one embodiment of the invention, microspheres are prepared from biodegradable polymers such as those described above, among others, using the following method steps: (a) dissolving one or more biodegradable polymers and, optionally, one or more optional agents (e.g., therapeutic agents, etc.) in methyl dichloroacetate, (b) combining the methyl dichloroacetate solution with an aqueous solution, for instance, water and one or more optional agents (e.g., one or more emulsion stabilizers such as polyvinyl alcohol, etc.), (c) emulsifying the mixture to achieve droplets containing the polymer and methyl dichloroacetate dispersed within the aqueous solution (i.e., the methyl dichloroacetate is used as the dispersed phase organic solvent of an oil-in-water emulsion) and (d) adding an ammonia solution to the emulsion, which rapidly cleaves the methyl dichloroacetate into water-soluble dichloroacetamide and methanol, transforming the emulsion droplets into hardened microspheres. See, e.g., H. Sah et al., *Macromolecular Rapid Communications*, 27 (2006) 1845-1851. As elsewhere herein the resulting microspheres can be used for various bulking, embolization and drug delivery procedures, for instance, bland embolization, transarterial chemoembolization (TACE), and drug eluting microspheres for disease states such as liver cancer, among many others. Some advantages of this method over the solvent evaporation method include one or more of the following, among others: (a) improved methods for incorporating into the microspheres additional desirable agents such as hydrophobic drugs (e.g. paclitaxel, its derivatives, etc.), porogens, other agents (e.g. radiopacifying agents, thrombogenic agents, etc.), (b) reduced time required to harden the microspheres, (c) improved methods for controlling the levels of residual solvent in the microspheres, (d) a reduction of the amount of aqueous continuous phase required, (e) simplified equipment for microsphere preparation, and (f) reduced emission of organic solvents to the atmosphere.

Regardless of the method of formation, the particles may then be washed, isolated, sized and lyophilized, as desired.

As noted above, in some embodiments, it is desirable to introduce one or more optional agents (e.g., therapeutic agents, radiopacifying agents, supplemental polymers, etc.) into the particles. Such optional agents can be incorporated at various stages of the production process, for example, before particle production (e.g., by covalently bonding the optional agent to the copolymer), during particle formation (e.g., as described above) or after particle formation (e.g., by placing particles in a solution that includes the optional agent). In the later case, in some embodiments, the particles may be dried by a suitable method, for example, by lyophilization (freeze drying), prior to placing them in the optional-agent-containing solution. In the rehydration process, the agent is drawn into the particles. The particle composition may be re-dried at this stage, if desired.

As another example, a therapeutic agent may be added by a medical practitioner to a particulate composition in accordance with the invention at the time of administration to a subject.

The particle compositions of the invention may be stored and transported in a sterile dry form. In addition to copolymers in accordance with the invention, the dry composition may also optionally contain additional agents, for example, selected from one or more of the following, among others: (a) tonicity adjusting agents such as sugars (e.g., dextrose, lactose, etc.), polyhydric alcohols (e.g., glycerol, propylene glycol, mannitol, sorbitol, etc.) and inorganic salts (e.g., potassium chloride, sodium chloride, etc.), among others, (b) suspension agents including various surfactants, wetting agents, and polymers (e.g., albumen, PEO, polyvinyl alcohol, block copolymers, etc.), among others, (c) imaging contrast agents (e.g., radiopacifying agents such as those found in Omnipaque™, Visipaque™, etc.), (d) pH adjusting agents including various buffer solutes, (e) therapeutic agents and (f) supplemental polymers. The dry composition may shipped, for example, in a syringe, catheter, vial, ampoule, or other container, and it may be mixed with a suitable liquid carrier (e.g. sterile water for injection, physiological saline, phosphate buffer, a solution containing an imaging contrast agent, etc.) prior to administration. In this way the concentration of the composition to be injected may be varied at will, depending on the specific application at hand, as desired by the health care practitioner in charge of the procedure. One or more containers of liquid carrier may also be supplied and shipped, along with the dry particles, in the form of a kit.

As long as excess degradation does not occur (which is related to polymer properties, solution properties, shelf-life requirements, etc.), the injectable particles may also be stored in a sterile suspension that contains water in addition to the particles themselves, as well as other optional agents such as one or more of the tonicity adjusting agents, suspension agents, contrast media, pH adjusting agents (e.g., for pH 5.5-7.5, among other possibilities), and therapeutic agents listed above, among others. The suspension may be stored, for example, in a syringe, catheter, vial, ampoule, or other container. The suspension may also be mixed with a suitable liquid carrier (e.g. sterile water for injection, physiological saline, phosphate buffer, a solution containing contrast agent, etc.) prior to administration, allowing the concentration of administered particles (as well as other optional agents) in the suspension to be reduced prior to injection, if so desired by the health care practitioner in charge of the procedure. One or more containers of liquid carrier may also be supplied to form a kit.

The amount of injectable particles within a suspension to be injected may be determined by those of ordinary skill in the art. The amount of particles may be limited by the fact that when the amount of particles in the composition is too low, too much liquid may be injected, possibly allowing particles to stray far from the site of injection, which may result in undesired embolization or bulking of vital organs and tissues. When the amount of particles is too great, the delivery device (e.g., catheter, syringe, etc.) may become clogged.

An effective amount of the particle compositions of the invention is, for example, (a) an amount sufficient to produce an occlusion or emboli at a desired site in the body, (b) an amount sufficient to achieve the degree of bulking desired (e.g., an amount sufficient to improve urinary incontinence, vesicourethral reflux, fecal incontinence, ISD or gastroesophageal reflux, or an amount sufficient for aesthetic improvement), or (c) an amount sufficient to locally treat a disease or condition. Effective doses may also be extrapolated from dose-response curves derived from animal model test systems, among other techniques.

In certain embodiments, the density of the aqueous phase that suspends the particles is close to that of the particles themselves, thereby promoting an even suspension. The density of the aqueous phase may be increased, for example, by increasing the amount of solutes that are dissolved in the aqueous phase, and vice versa.

As noted above, permanent or temporary occlusion of blood vessels is useful for managing various diseases and conditions. For example, fibroids, also known as leiomyoma, leiomyomata or fibromyoma, are the most common benign tumors of the uterus. These non-cancerous growths are present in significant fraction of women over the age of 35. In most cases, multiple fibroids are present, often up to 50 or more. Fibroids can grow, for example, within the uterine wall ("intramural" type), on the outside of he uterus ("subserosal" type), inside the uterine cavity ("submucosal" type), between the layers of broad ligament supporting the uterus ("interligamentous" type), attached to another organ ("parasitic" type), or on a mushroom-like stalk ("pedunculated" type). Fibroids may range widely in size, for example, from a few millimeters to 40 centimeters. In some women, fibroids can become enlarged and cause excessive bleeding and pain. While fibroids have been treated in the past by surgical removal of the fibroids (myomectomy) or by removal of the uterus (hysterectomy), recent advances in uterine embolization now offer a nonsurgical treatment. Thus, injectable compositions in accordance with the present invention can be used to treat uterine fibroids.

Methods for treatment of fibroids by embolization are well known to those skilled in the art (see, e.g., Pub. No. US 2003/0206864 to Mangin and the references cited therein). Uterine embolization is aimed at starving fibroids of nutrients. Numerous branches of the uterine artery may supply uterine fibroids. In the treatment of fibroids, embolization of the entire uterine arterial distribution network is often preferred. This is because it is difficult to selectively catheterize individual vessels supplying only fibroids, the major reason being that there are too many branches for catheterization and embolization to be performed in an efficient and timely manner. Also, it is difficult to tell whether any one vessel supplies fibroids rather than normal myometrium. In many women, the fibroids of the uterus are diffuse, and embolization of the entire uterine arterial distribution affords a global treatment for every fibroid in the uterus.

In a typical procedure, a catheter is inserted near the uterine artery by the physician (e.g., with the assistance of a guide wire). Once the catheter is in place, the guide wire is removed and contrast agent is injected into the uterine artery. The patient is then subjected to fluoroscopy or X-rays. In order to create an occlusion, an embolic agent is introduced into the uterine artery via catheter. The embolic agent is carried by the blood flow in the uterine artery to the vessels that supply the fibroid. The particles flow into these vessels and clog them, thus disrupting the blood supply to the fibroid. In order for the physician to view and follow the occlusion process, contrast agent may be injected subsequent to infusion of the embolic agent. Treatment may be enhanced in the present invention by including a therapeutic agent (e.g., toxin, ablation agent, antineoplastic/antiproliferative/anti-miotic agent, etc.) in the particulate composition.

Controlled, selective obliteration of the blood supply to tumors is also used in treating solid tumors such as renal carcinoma, bone tumor and liver cancer, among various others. The idea behind this treatment is that preferential blood flow toward a tumor will carry the embolization agent to the tumor thereby blocking the flow of blood which supplies nutrients to the tumor, causing it to shrink. Embolization may be conducted as an enhancement to chemotherapy or radiation therapy. Treatment may be enhanced in the present invention by including a therapeutic agent (e.g., antineoplastic/antiproliferative/anti-miotic agent, toxin, ablation agent, etc.) in the particulate composition.

Particle compositions in accordance with the invention may also be used to treat various other diseases, conditions and disorders, including treatment of the following: arteriovenous fistulas and malformations including, for example, aneurysms such as neurovascular and aortic aneurysms, pulmonary artery pseudoaneurysms, intracerebral arteriovenous fistula, cavernous sinus dural arteriovenous fistula and arterioportal fistula, chronic venous insufficiency, varicocele, pelvic congestion syndrome, gastrointestinal bleeding, renal bleeding, urinary bleeding, varicose bleeding, uterine hemorrhage, and severe bleeding from the nose (epistaxis), as well as preoperative embolization (to reduce the amount of bleeding during a surgical procedure) and occlusion of saphenous vein side branches in a saphenous bypass graft procedure, among other uses. As elsewhere herein, treatment may be enhanced in the present invention by including a therapeutic agent in the particulate composition.

Particle compositions in accordance with the invention may also be used in tissue bulking applications, for example, as augmentative materials in the treatment of urinary incontinence, vesicourethral reflux, fecal incontinence, intrinsic sphincter deficiency (ISD) or gastro-esophageal reflux disease, or as augmentative materials for aesthetic improvement. For instance, a common method for treating patients with urinary incontinence is via periurethral or transperineal injection of a bulking material. In this regard, methods of injecting bulking agents commonly require the placement of a needle at a treatment region, for example, periurethrally or transperineally. The bulking agent is injected into a plurality of locations, assisted by visual aids, causing the urethral lining to coapt. In some cases, additional applications of bulking agent may be required. Treatment may be enhanced by including a therapeutic agent (e.g., proinflammatory agents, sclerosing agents, etc.) in the particulate composition.

The present invention encompasses various ways of administering the particulate compositions of the invention to effect embolization, bulking or other procedure benefiting from therapeutic agent release. One skilled in the art can determine the most desirable way of administering the particles depending on the type of treatment and the condition of the patient, among other factors. Methods of administration include, for example, percutaneous techniques as well as other effective routes of administration. For example, the particulate compositions of the invention may be delivered through a syringe or through a catheter, for instance, a Tracker® microcatheter (Boston Scientific, Natick, Mass., USA), which can be advanced over a guidewire, a steerable microcatheter, or a flow-directed microcatheter (MAGIC, Balt, Montomorency, France).

Various aspects of the invention relating to the above are enumerated in the following paragraphs:

Aspect 1. Injectable polymeric particles comprising a copolymer that comprises (a) a hydroxy-acid-based repeat unit selected from a mono(hydroxy acid) unit and a poly (hydroxy acid) unit, (b) an alkyl-ether-based repeat unit selected from a mono(alkyl ether) unit and a poly(alkyl ether) unit, and (c) an acid-based repeat unit selected from a unit comprising multiple carboxylic acid groups, a unit comprising multiple acid chloride groups, and a cyclic acid anhydride unit, wherein 95 vol % of the particles have a longest linear cross-sectional dimension between 40 μm and 5000 μm.

Aspect 2. The injectable polymeric particles of Aspect 1, wherein the alkyl-ether-based repeat unit comprises one or more alkyl ether monomers selected from ethylene oxide, propylene oxide and butylene oxide.

Aspect 3. The injectable polymeric particles of Aspect 1, wherein the alkyl-ether-based repeat unit is of the formula $-[R_1-O]_n-$, where in the preceding formula $R_1$ is C1-C10 linear or branched alkyl and n is an integer of 1 or more.

Aspect 4. The injectable polymeric particles of Aspect 1, wherein the hydroxy-acid-based repeat unit comprises one or more hydroxy acid monomers selected from branched and unbranched C1-C10 hydroxy acids.

Aspect 5. The injectable polymeric particles of Aspect 1, wherein the hydroxy-acid-based repeat unit comprises one or more hydroxy acid monomers selected from glycolic acid and lactic acid.

Aspect 6. The injectable polymeric particles of Aspect 1, wherein the hydroxy-acid-based repeat unit is of the formula,

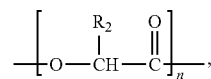

where in the preceding formula $R_2$ is H or C1-C10 linear or branched alkyl and n is an integer of 1 or more.

Aspect 7. The injectable polymeric particles of Aspect 1, wherein the acid-based repeat unit is selected from dicarboxylic acids, tricarboxylic acids, dicarboxylic acid chlorides, tricarboxylic acid chlorides, and cyclic acid anhydrides.

Aspect 8. The injectable polymeric particles of Aspect 1, wherein the acid-based repeat unit is of the formula,

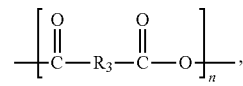

where in the preceding formula n is one and $R_3$ is selected from (a) a bond and (b) C1-C10 linear or branched alkyl, which may be either unsubstituted or substituted with one or more halogen atoms.

Aspect 9. The injectable polymeric particles of Aspect 8, wherein the one or more halogen atoms comprise bromine atoms, iodine atoms, or a combination thereof.

Aspect 10. The injectable polymeric particles of Aspect 1, wherein the particles do not contain an ionic or covalent cross-linking agent.

Aspect 11. The injectable polymeric particles of Aspect 1, wherein the copolymer further comprises bromine atoms, iodine atoms or a combination thereof.

Aspect 12. The injectable polymeric particles of Aspect 1, wherein the injectable particles are spherical.

Aspect 13. The injectable polymeric particles of Aspect 1, wherein the particles are porous particles.

Aspect 14. The injectable polymeric particles of Aspect 1, wherein 95 vol % of the particles have a longest linear cross-sectional dimension between 100 and 1200 μm.

Aspect 15. The injectable polymeric particles of Aspect 1, wherein the copolymer further comprises a group that chelates a charged radioisotope.

Aspect 16. The injectable polymeric particles of Aspect 1, further comprising a therapeutic agent selected from toxins, thrombogenic agents, antineoplastic agents, ablation agents, proinflammatory agents and sclerosing agents.

Aspect 17. The injectable polymeric particles of Aspect 1, further comprising a therapeutic agent that non-covalently binds to the particles by electrostatic interactions with binding groups in the particles.

Aspect 18. The injectable polymeric particles of Aspect 17, wherein the therapeutic agent is a charged radioisotope and the particles comprise ligands that form coordination complexes with the charged radioisotope.

Aspect 19. The injectable particles of Aspect 1, wherein the hydroxy-acid-based repeat unit:alkyl-ether-based repeat unit: acid-based repeat unit ratio is 1:1:1.

Aspect 20. The injectable particles of Aspect 1, wherein the hydroxy-acid-based repeat unit:alkyl-ether-based repeat unit: acid-based repeat unit ratio is 2:1:1.

Aspect 21. An injectable medical composition comprising the particles of Aspect 1.

Aspect 22. The injectable medical composition of Aspect 21, comprising a tonicity adjusting agent.

Aspect 23. The injectable medical composition of Aspect 21, wherein the injectable medical composition is disposed within a glass container or a preloaded medical device.

Aspect 24. A method of embolization comprising injecting the injectable medical composition of Aspect 21 into a patient.

Aspect 25. A method of tissue bulking comprising injecting the injectable medical composition of Aspect 21 into a patient.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. Injectable polymeric particles comprising a copolymer that comprises
    (a) a hydroxy-acid-based repeat unit selected from a mono (hydroxy acid) unit and a poly(hydroxy acid) unit,
    (b) an alkyl-ether-based repeat unit selected from a mono (alkyl ether) unit and a poly(alkyl ether) unit, and
    (c) an acid-based repeat unit selected from a unit comprising multiple carboxylic acid groups, a unit comprising multiple acid chloride groups, and a cyclic acid anhydride unit, wherein said copolymer further comprises bromine atoms, iodine atoms, or a combination thereof, and wherein 95 vol % of the particles have a longest linear cross-sectional dimension between 40 μm and 5000 μm.

2. The injectable polymeric particles of claim 1, wherein said alkyl-ether-based repeat unit comprises one or more alkyl ether monomers selected from ethylene oxide, propylene oxide and butylene oxide.

3. The injectable polymeric particles of claim 1, wherein said alkyl-ether-based repeat unit is of the formula $-[R_1-O]_n-$, where in the preceding formula $R_1$ is C1-C10 linear or branched alkyl and n is an integer of 1 or more.

4. The injectable polymeric particles of claim 1, wherein said hydroxy-acid-based repeat unit comprises one or more hydroxy acid monomers selected from branched and unbranched C1-C10 hydroxy acids.

5. The injectable polymeric particles of claim 1, wherein said hydroxy-acid-based repeat unit comprises one or more hydroxy acid monomers selected from glycolic acid and lactic acid.

6. The injectable polymeric particles of claim 1, wherein said hydroxy-acid-based repeat unit is of the formula,

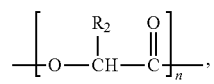

where in the preceding formula $R_2$ is H or C1-C10 linear or branched alkyl and n is an integer of 1 or more.

7. The injectable polymeric particles of claim 1, wherein said acid-based repeat unit is selected from dicarboxylic acids, tricarboxylic acids, dicarboxylic acid chlorides, tricarboxylic acid chlorides, and cyclic acid anhydrides.

8. The injectable polymeric particles of claim 1, wherein said acid-based repeat unit is of the formula,

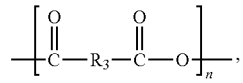

where in the preceding formula n is one and $R_3$ is selected from (a) a bond and (b) C1-C10 linear or branched alkyl, which may be either unsubstituted or substituted with one or more halogen atoms.

9. The injectable polymeric particles of claim 8, wherein said one or more halogen atoms comprise bromine atoms, iodine atoms, or a combination thereof.

10. The injectable polymeric particles of claim 1, wherein said particles do not contain an ionic or covalent cross-linking agent.

11. The injectable polymeric particles of claim 1, wherein said injectable particles are spherical.

12. The injectable polymeric particles of claim 1, wherein said particles are porous particles.

13. The injectable polymeric particles of claim 1, wherein 95 vol % of said particles have a longest linear cross-sectional dimension between 100 and 1200 μm.

14. The injectable polymeric particles of claim 1, wherein said copolymer further comprises a group that chelates a charged radioisotope.

15. The injectable polymeric particles of claim 1, further comprising a therapeutic agent selected from toxins, thrombogenic agents, antineoplastic agents, ablation agents, proinflammatory agents and sclerosing agents.

16. The injectable polymeric particles of claim 1, further comprising a therapeutic agent that non-covalently binds to the particles by electrostatic interactions with binding groups in the particles.

17. The injectable polymeric particles of claim 16, wherein said therapeutic agent is a charged radioisotope and said particles comprise ligands that form coordination complexes with the charged radioisotope.

18. The injectable particles of claim 1, wherein said hydroxy-acid-based repeat unit:alkyl-ether-based repeat unit: acid-based repeat unit ratio is 1:1:1.

19. The injectable particles of claim 1, wherein said hydroxy-acid-based repeat unit:alkyl-ether-based repeat unit: acid-based repeat unit ratio is 2:1:1.

20. An injectable medical composition comprising the particles of claim 1.

21. The injectable medical composition of claim 20, comprising a tonicity adjusting agent.

22. The injectable medical composition of claim 20, wherein said injectable medical composition is disposed within a glass container or a preloaded medical device.

23. A method of embolization comprising injecting the injectable medical composition of claim 20 into a patient.

24. A method of tissue bulking comprising injecting the injectable medical composition of claim 20 into a patient.

* * * * *